US008337426B2

(12) United States Patent
Nycz

(10) Patent No.: US 8,337,426 B2
(45) Date of Patent: Dec. 25, 2012

(54) METHOD AND APPARATUS FOR ALIGNING AND SECURING AN IMPLANT RELATIVE TO A PATIENT

(75) Inventor: Jeffrey H. Nycz, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 626 days.

(21) Appl. No.: 12/486,842

(22) Filed: Jun. 18, 2009

(65) Prior Publication Data
US 2010/0249796 A1 Sep. 30, 2010

Related U.S. Application Data

(63) Continuation-in-part of application No. 12/358,664, filed on Mar. 24, 2009, now Pat. No. 8,167,823.

(51) Int. Cl.
| | |
|---|---|
| A61B 5/103 | (2006.01) |
| A61B 5/117 | (2006.01) |
| A61B 17/58 | (2006.01) |
| A61B 17/60 | (2006.01) |
| A61F 5/00 | (2006.01) |
| A61F 2/00 | (2006.01) |
| A61F 2/32 | (2006.01) |

(52) U.S. Cl. ............ 600/587; 600/595; 606/87; 606/91; 606/93; 606/99; 606/102; 623/22.11; 623/22.12

(58) Field of Classification Search ........... 600/587, 600/595; 606/87, 91, 93, 99, 102; 623/22.11, 623/22.12
See application file for complete search history.

(56) References Cited

U.S. PATENT DOCUMENTS

| | | | |
|---|---|---|---|
| 5,725,592 | A | 3/1998 | White et al. |
| 5,769,092 | A | 6/1998 | Williamson, Jr. |
| 5,880,976 | A | 3/1999 | DiGioia, III et al. |
| 5,902,340 | A | 5/1999 | White et al. |
| 5,995,738 | A | 11/1999 | DiGioia, III et al. |
| 6,002,859 | A | 12/1999 | DiGioia, III et al. |
| 6,447,448 | B1 | 9/2002 | Ishikawa et al. |
| 6,583,630 | B2 | 6/2003 | Mendes et al. |

(Continued)

FOREIGN PATENT DOCUMENTS

EP      1563810 A1    8/2005

(Continued)

OTHER PUBLICATIONS

Non Final Office Action mailed Jun. 30, 2011 in U.S. Appl. No. 12/358,664.

(Continued)

*Primary Examiner* — Sean Dougherty
(74) *Attorney, Agent, or Firm* — Harness, Dickey

(57) ABSTRACT

A surgical instrument for implanting a prosthetic member. The instrument includes an orientation sensor that detects an initial orientation of the prosthetic member and an implanting orientation of the prosthetic member. The instrument further includes a memory module and an input device that receives a user input to transfer the initial orientation detected by the orientation sensor into the memory module for storage. Furthermore, the instrument includes an orientation feedback device that selectively provides an orientation feedback signal to a user. Moreover, the instrument includes a controller that causes the orientation feedback device to provide the orientation feedback signal when the implanting orientation detected by the orientation sensor is substantially equal to the initial orientation stored in the memory module.

22 Claims, 6 Drawing Sheets

U.S. PATENT DOCUMENTS

| | | |
|---|---|---|
| 6,610,096 B2 | 8/2003 | MacDonald |
| 6,702,821 B2 | 3/2004 | Bonutti |
| 6,711,431 B2 | 3/2004 | Sarin et al. |
| 6,746,487 B2 | 6/2004 | Scifert et al. |
| 6,810,753 B2 | 11/2004 | Valdevit et al. |
| 6,821,299 B2 | 11/2004 | Kirking et al. |
| 6,871,549 B2 | 3/2005 | Serra et al. |
| 7,001,393 B2 | 2/2006 | Schwenke et al. |
| 7,331,965 B2 | 2/2008 | Nielsen |
| 7,338,499 B1 | 3/2008 | Kuczynski et al. |
| 7,377,182 B2 | 5/2008 | Serra et al. |
| 7,458,989 B2 | 12/2008 | Banks et al. |
| 7,542,791 B2 | 6/2009 | Mire et al. |
| 7,559,931 B2 | 7/2009 | Stone |
| 7,636,595 B2 | 12/2009 | Marquart et al. |
| 7,660,623 B2 | 2/2010 | Hunter et al. |
| 7,780,681 B2 | 8/2010 | Sarin et al. |
| 8,057,482 B2 * | 11/2011 | Stone et al. .......... 606/102 |
| 8,109,942 B2 * | 2/2012 | Carson .......... 606/130 |
| 2002/0077540 A1 | 6/2002 | Kienzle |
| 2002/0107523 A1 | 8/2002 | Naughton et al. |
| 2003/0153829 A1 | 8/2003 | Sarin et al. |
| 2003/0181987 A1 | 9/2003 | Muirhead-Allwood |
| 2004/0034302 A1 | 2/2004 | Abovitz et al. |
| 2004/0044295 A1 | 3/2004 | Reinert et al. |
| 2004/0097952 A1 | 5/2004 | Sarin et al. |
| 2004/0102792 A1 | 5/2004 | Sarin et al. |
| 2004/0117026 A1 | 6/2004 | Tuma et al. |
| 2004/0171924 A1 | 9/2004 | Mire et al. |
| 2004/0230199 A1 | 11/2004 | Jansen et al. |
| 2004/0243148 A1 | 12/2004 | Wasielewski |
| 2004/0254584 A1 | 12/2004 | Sarin et al. |
| 2005/0021044 A1 | 1/2005 | Stone et al. |
| 2005/0065617 A1 | 3/2005 | Moctezuma de la Barrera et al. |
| 2005/0109855 A1 * | 5/2005 | McCombs .......... 236/100 |
| 2005/0113659 A1 * | 5/2005 | Pothier et al. .......... 600/372 |
| 2005/0143828 A1 | 6/2005 | Collins et al. |
| 2005/0203384 A1 | 9/2005 | Sati et al. |
| 2005/0234332 A1 * | 10/2005 | Murphy .......... 600/426 |
| 2005/0234468 A1 * | 10/2005 | Carson .......... 606/96 |
| 2005/0245808 A1 * | 11/2005 | Carson .......... 600/407 |
| 2005/0251026 A1 | 11/2005 | Stone |
| 2006/0094958 A1 | 5/2006 | Marquart et al. |
| 2006/0095047 A1 | 5/2006 | de la Barrera |
| 2007/0149981 A1 | 6/2007 | Bhattacharyya |
| 2007/0179739 A1 | 8/2007 | Donofrio et al. |
| 2008/0133016 A1 | 6/2008 | Heinz |
| 2008/0249395 A1 | 10/2008 | Shachar et al. |
| 2009/0099570 A1 | 4/2009 | Paradis et al. |
| 2009/0138019 A1 | 5/2009 | Wasielewski |
| 2009/0234217 A1 | 9/2009 | Mire et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2010/0016705 A1 | 1/2010 | Stone |
| 2010/0076505 A1 | 3/2010 | Borja |
| 2010/0100011 A1 | 4/2010 | Roche |
| 2010/0137871 A1 | 6/2010 | Borja |
| 2010/0249657 A1 | 9/2010 | Nycz et al. |
| 2011/0060339 A1 * | 3/2011 | de Wekker .......... 606/80 |

FOREIGN PATENT DOCUMENTS

| | | |
|---|---|---|
| WO | WO-2004030556 A2 | 4/2004 |
| WO | WO-2004112610 A2 | 12/2004 |
| WO | WO-2007147235 A1 | 12/2007 |

OTHER PUBLICATIONS

"c2a—Taper ceramic-on-ceramic articulation," Surgical Technique brochure. (2006, 2007) Biomet Orthopedics, Inc. (21 pages).

"Vision Acetabular Surgical Technique," brochure. 2001. Biomet Orthopedics, Inc. (16 pages).

International Search Report mailed Jun. 11, 2010 for PCT/US2010/028325 claiming benefit of U.S. Appl. No. 12/486,842, filed Jun. 18, 2009; which claims benefit of U.S. Appl. No. 12/358,664, filed Mar. 24, 2009.

International Preliminary Report mailed Oct. 6, 2011.

* cited by examiner

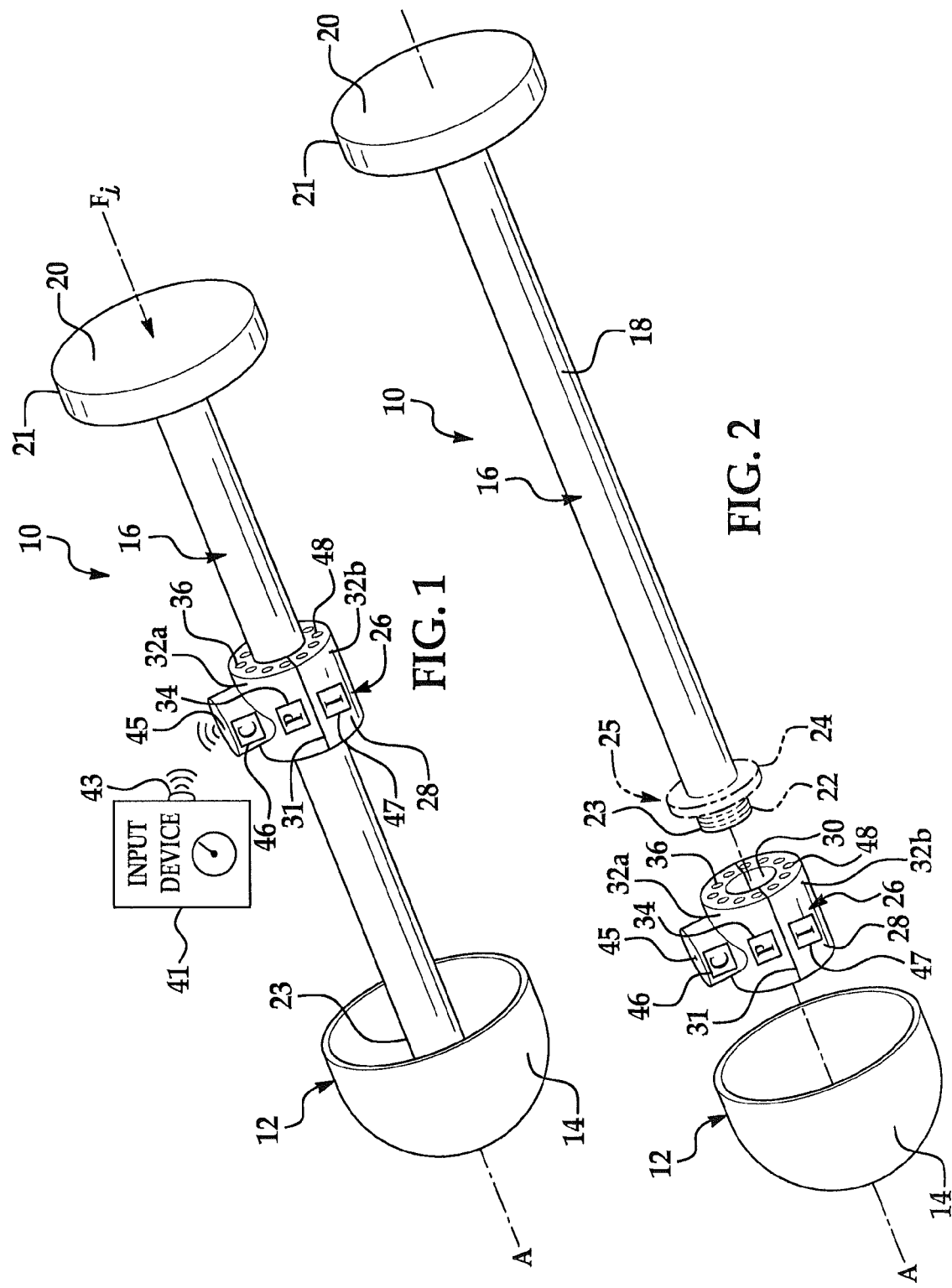

ers. Furthermore, the

METHOD AND APPARATUS FOR ALIGNING AND SECURING AN IMPLANT RELATIVE TO A PATIENT

CROSS-REFERENCE TO RELATED APPLICATION

This application is a continuation-in-part of U.S. patent application Ser. No. 12/358,664 filed on Mar. 24, 2009, the disclosure of which is incorporated by reference herein in its entirety.

FIELD

The following relates to an implantable prosthesis and, more particularly, to a method and apparatus for aligning and securing an implant relative to a patient.

BACKGROUND

The statements in this section merely provide background information related to the present disclosure and may not constitute prior art.

Prosthetic joints can reduce pain due to arthritis, deterioration, deformation, and the like, and can improve mobility in the joint. Oftentimes, prosthetic joint assemblies include certain implantable prosthetic members that are fixed to the patient's anatomy. For instance, prosthetic hip joint assemblies often include an acetabular cup that is implanted and fixed to the patient's pelvis within the acetabulum. Once properly fixed to the pelvis, a liner may be received by the cup, and a femoral component may be moveably coupled within the liner.

Medical professionals often use impactor tools to implant and fix prosthetic members to the patient's anatomy. In the case of the acetabular cup, for instance, the surgeon may attach the cup to one end of the impactor tool and strike or otherwise apply a load to the impactor tool to drive the cup into the acetabulum. Then, the impactor tool is removed from the cup, leaving the cup in the desired location and orientation within the acetabulum. Fasteners can also be used to further secure the cup to the pelvis.

To ensure that the prosthetic member will be oriented in a desired position during the implantation procedure, the surgeon typically moves the impactor tool to a predetermined orientation relative to the patient's anatomy and applies the load while maintaining the impactor tool at this predetermined orientation. Certain measuring devices (e.g., goniometers, etc.) have been proposed for these purposes. Specifically, in the case of implanting an acetabular cup, the surgeon might orient the impactor tool such that the load axis is at a predetermined inclination angle relative to the median plane of the patient's body and/or such that the load axis is at a predetermined anteversion angle relative to the coronal plane of the patient's body. Thus, as the load is applied to the impactor tool, the cup is driven along and fixed at the predetermined inclination angle and/or the predetermined anteversion angle within the acetabulum.

However, measuring the orientation of the impactor tool in this manner can be tedious, time consuming, inconvenient and inaccurate. For instance, surgeons typically must repeatedly measure the orientation of the impactor tool because applying one or more loads to the impactor tool could move the impactor tool out of alignment with the predetermined orientation. Additionally, the impactor tool can be improperly aligned inadvertently due to human error. Furthermore, the goniometer or other measurement device is oftentimes separate from the impactor tool, and thus, the surgeon may need two hands to hold the impactor tool and measure its orientation. Also, blood, tissue or other matter can obscure the surgeon's ability to read the measurement device, which can lead to inaccuracies.

In addition, it can be difficult to know when the implantable prosthetic member has been driven far enough into bone or other tissue. For instance, a surgeon typically drives the acetabular cup far enough into the acetabulum to seat the cup against cancellous bone. However, it can be difficult to visually confirm that the cup is seated against the cancellous bone, and thus, surgeons typically rely on audible, tactile, or other non-visual cues to know the cup has been properly seated. For example, the surgeon repeatedly applies loads to the impactor tool to progressively drive the cup into the acetabulum until the surgeon hears a sound indicating that the cup is seated against cancellous bone. In other cases, loads are applied to the impactor tool until the surgeon feels a certain degree of bounce-back (i.e., displacement of the tool in a direction opposite to the vector of the impact force on the tool) indicating that the cup is seated against cancellous bone. However, the accuracy of these methods can be improved.

SUMMARY

A surgical instrument is disclosed for implanting a prosthetic member. The instrument includes an orientation sensor that detects an initial orientation of the prosthetic member and an implanting orientation of the prosthetic member. The instrument further includes a memory module and an input device that receives a user input to transfer the initial orientation detected by the orientation sensor into the memory module for storage. Furthermore, the instrument includes an orientation feedback device that selectively provides an orientation feedback signal to a user. Moreover, the instrument includes a controller that causes the orientation feedback device to provide the orientation feedback signal when the implanting orientation detected by the orientation sensor is substantially equal to the initial orientation stored in the memory module.

In addition, a method of implanting a prosthetic member is disclosed that includes detecting an initial orientation of the prosthetic member. The method also includes saving the initial orientation into a memory module as a result of receiving a user input. Furthermore, the method includes detecting an implanting orientation of the prosthetic member and providing an orientation feedback signal when the implanting orientation of the prosthetic member is substantially equal to the initial orientation.

In another aspect, a prosthesis implantation system for implanting a prosthetic member is disclosed that includes a trial prosthetic acetabular cup defining a trial axis. The system also includes a primary prosthetic acetabular cup defining a primary axis. Moreover, the system includes an impactor tool that removably couples to the primary prosthetic acetabular cup and transfers a load along a load axis to implant the primary prosthetic acetabular cup. In addition, the system includes a prosthesis implanting apparatus having a housing that defines a housing axis. The housing is removably coupled to the trial prosthetic acetabular cup to position the housing axis at a known orientation relative to the trial axis, and the housing is alternatively and removably coupled to the impactor tool to position the housing axis at a known orientation relative to the primary axis. The implanting apparatus further includes an orientation sensor that detects an initial orientation of the housing axis and an implanting orientation of the housing axis relative to a direction of gravity. Additionally, the implanting apparatus includes a memory module and an input device that receives a user input to transfer the initial orientation detected by the orientation sensor into the memory module for storage. Furthermore, the implanting apparatus includes an orientation feedback device that selectively provides an orientation feedback signal and a controller that causes the orientation feedback device to provide the orientation feedback signal when the prosthesis implanting apparatus is coupled to the impactor tool and when the implanting orientation is substantially equal to the initial orientation stored in the memory module.

In still another aspect, a method of implanting a primary prosthetic acetabular cup is disclosed that includes removably coupling a prosthesis implanting apparatus with an orientation sensor to a trial prosthetic acetabular cup. The method further includes detecting an initial orientation of the trial prosthetic acetabular cup with the orientation sensor and saving the initial orientation into a memory module as a result of receiving a user input. Furthermore, the method includes removing the prosthesis implanting apparatus from the trial prosthetic acetabular cup, removably coupling an impactor tool to the primary prosthetic acetabular cup, and removably coupling the prosthesis implanting apparatus to the impactor tool. In addition, the method includes detecting an implanting orientation of the prosthesis implanting apparatus with the orientation sensor. Also, the method includes providing an orientation feedback signal when the implanting orientation is substantially equal to the initial orientation and implanting the primary prosthetic acetabular cup at the initial orientation.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1 is a perspective view of an implanting assembly according to the present disclosure;

FIG. 2 is an exploded view of the implanting assembly of FIG. 1;

DETAILED DESCRIPTION

Figures 3, 4:
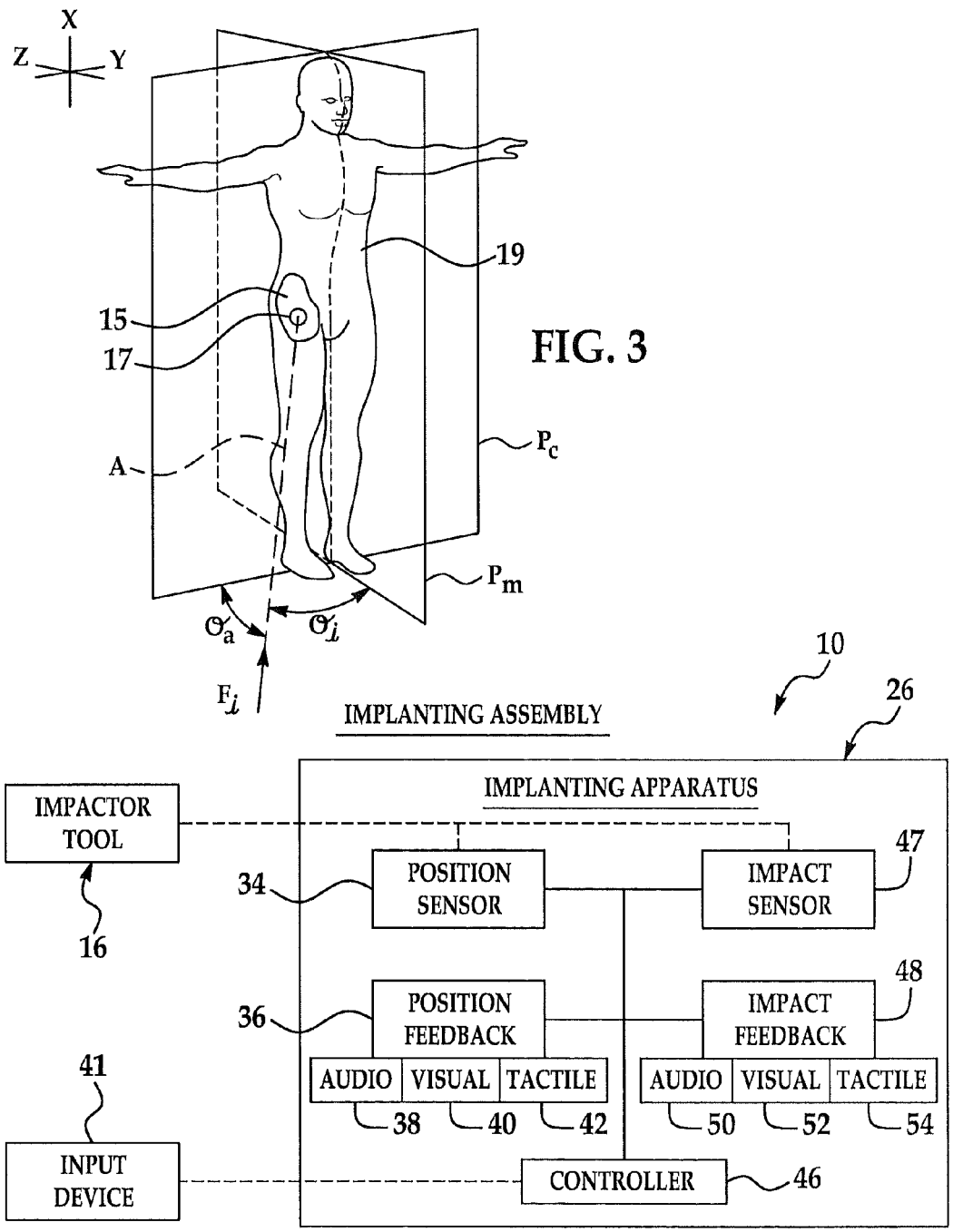
FIG. 3 is a perspective view of a patient, various reference planes, and a load axis of the implanting assembly of FIG. 1 relative to the various reference planes of the patient.
FIG. 4 is a schematic view of the implanting assembly of FIG. 1.

The following description is merely exemplary in nature and is not intended to limit the present disclosure, application, or uses. It should be understood that throughout the drawings, corresponding reference numerals indicate like or corresponding parts and features.

Referring initially to FIGS. 1, 2 and 4, an exemplary embodiment of an implanting assembly 10 is illustrated. As will be discussed, the implanting assembly 10 can be used for implanting any suitable prosthetic member 12. In the embodiments illustrated, the implanting assembly 10 is used to implant an acetabular cup 14. The acetabular cup 14 can be of any suitable type. Specifically, the implanting assembly 10 can be used to implant the acetabular cup 14 in a pelvis 15, within the acetabulum 17, of a patient 19 (FIG. 3). Thus, the implanting assembly 10 can be used in a process for replacing a hip joint with a prosthetic hip joint assembly.

The implanting assembly 10 can include an impactor tool 16, as shown in FIGS. 1 and 2. Generally, the impactor tool 16 can include an elongated shaft 18 having an enlarged striking plate or head 20 at a proximal or first end 21. The shaft 18 can be longitudinally straight so as to define an axis A. Alternately, the shaft 18 can be angled or curved to account for various anatomical shapes, surgical procedures, etc. Also, the enlarged head 20 can be substantially disk shaped and centered on the axis A. The distal or second end 23 of the shaft 18 can include a coupling mechanism 25 as shown in phantom in FIG. 2. In some embodiments, the coupling mechanism 25 can include a thread (shown in phantom at 22) and a projection (shown in phantom at 24). The thread 22 can enable the shaft 18 to be removably coupled to the acetabular cup 14 in a corresponding threaded hole (not shown) in the acetabular cup 14. Also, the projection 24 can abut the acetabular cup 14 for transferring loads from the shaft 18 to the acetabular cup 14, as will be described in greater detail below. It will be appreciated, however, that the impactor tool 16 can be removably coupled to the acetabular cup 14 in any suitable fashion. Furthermore, the impactor tool 16 can be coupled to the acetabular cup 14 such that the shaft 18 and the acetabular cup 14 both extend along the axis A.

As will be described, in order to implant the acetabular cup 14 in the patient 19, a load $F_i$ (FIG. 1) is applied to the head 20 of the impactor tool 16. The surgeon can apply the load $F_i$ with a mallet or other manual tool or with an automated tool. The shaft 18, in turn, transfers the load $F_i$ along the axis A to the acetabular cup 14. Thus, the acetabular cup 14 is driven progressively into the acetabulum 17 of the pelvis 15 of the patient 19 (FIG. 3) with each application of the load $F_i$.

It will be appreciated that the load $F_i$ transfers along the axis A to the acetabular cup 14. Thus, the axis A corresponds to the load axis A of the implanting assembly 10. It will also be appreciated that the impactor tool 16 could include a curved or offset axis A and that the load $F_i$ could be a rotational (i.e., angular) load without departing from the scope of the present disclosure.

The implanting assembly 10 can also include an implanting apparatus 26 (FIGS. 1, 2 and 4). As shown in FIGS. 1 and 2, the implanting apparatus 26 can include a housing 28. The housing 28 can be operatively coupled to the impactor tool 16. In some embodiments, the housing 28 can be removably coupled to the shaft 18 of the impactor tool 16 such that the implanting apparatus 26 extends substantially parallel to the axis A of the shaft 18. Specifically, the housing 28 can be substantially cylindrical in shape with a passage 30 extending parallel and concentric to the axis A. The passage 30 receives the shaft 18 to fixedly couple the housing 28 to the tool 16 in a fixed position relative to the axis A.

Furthermore, the housing 28 can include a seam 31 extending substantially parallel to the axis A. The seam 31 separates a first portion 32a from a second portion 32b of the housing 28. Thus, the first and second portions 32a, 32b can separate along the seam 31 to remove the housing 28 from the shaft 18. In some embodiments, the housing 28 can have a clam shell design with a hinge (not shown) for hingeably attaching the first and second portions 32a, 32b of the housing 28.

It will be appreciated that the housing 28 can fix to the shaft 18 in any suitable fashion, such as an interference fit, a taper lock between the shaft 18 and the inner surface of the passage 30, and the like. Also, the shaft 18 can include a recess (not shown) that receives the housing 28 such that the housing 28 is in a fixed position relative to the axis A. Accordingly, the implanting apparatus 26 can removably couple to preexisting, commercially available impactor tools 16, such as a Ring-Loc® Inserter (Part No. S313141) or a Magnum Inserter (Part No. 313131), commercially available from Biomet, Inc. of Warsaw, Ind.

Furthermore, it will be appreciated that the implanting apparatus 26 can be operatively coupled to the impactor tool 16 at any suitable location, including the head 20. It will also be appreciated that the seam 31 is optional, and the implanting apparatus 26 can be configured to slide on to the shaft 18 in a direction substantially parallel to the axis A (see FIG. 2). In addition, it will be appreciated that the implanting apparatus 26 can be integrally coupled to the impactor tool 16 such that the implanting apparatus 26 and the impactor tool 16 are monolithic. For instance, the implanting apparatus 26 can be incorporated directly in the shaft 18 and/or the head 20 or any other suitable portion of the tool 16. Also, in some embodiments, the implanting apparatus 26 may be configured so that the apparatus 26 can be operably coupled to surgical tools other than an implanting apparatus 26 for use in any other suitable surgical procedure.

As shown in FIGS. 1, 2 and 4, the implanting apparatus 26 can include an orientation sensor 34. The orientation sensor 34 can be encapsulated within the housing 28. In other embodiments, the orientation sensor 34 is remote from the impactor tool 16. As will be discussed, the orientation sensor 34 can detect an actual orientation of the impactor tool 16. More specifically, the orientation sensor 34 can be an accelerometer that is able to detect the orientation of the impactor tool 16 relative to a reference vector. In some embodiments, for instance, the orientation sensor 34 detects the vector of the force of gravity as a reference vector to detect the orientation of the impactor tool 16 in space and relative to the patient. More specifically, the orientation sensor 34 detects the orientation of the axis A relative to the vector of the force of gravity to detect the orientation of the tool 16. In some embodiments, the orientation sensor 34 detects acceleration about three separate orthogonal axes X, Y, Z (FIG. 3) in order to detect the orientation of the impactor tool 16. Specifically, the orientation sensor 34 detects the orientation of the axis A relative to the coordinate system X, Y, Z, as will be discussed in greater detail below. It will be appreciated that the orientation sensor 34 could be of any suitable type other than an accelerometer. Also, it will be appreciated that the orientation sensor 34 can be an accelerometer that detects accelerations about any number (e.g., two) of axes.

Furthermore, the implanting apparatus 26 can include an orientation feedback device 36. The feedback device 36 can be encapsulated within the housing 28, or in other embodiments, the feedback device 36 is remote from the housing 28. As will be described, the orientation feedback device 36 can selectively provide an orientation feedback signal when the actual orientation of the impactor tool 16 is substantially equal to a predetermined target orientation. Accordingly, as will be described in greater detail below, the feedback signal provided by the orientation feedback device 36 automatically indicates to the surgeon that the impactor tool 16 is in the target orientation such that the cup 14 can be properly positioned and implanted for added convenience and accuracy.

As represented in FIG. 4, the orientation feedback device 36 can include an audible feedback device 38 that emits an audible feedback signal. For instance, the audible feedback device 38 can include a speaker that emits a preprogrammed sound when the impactor tool 16 is in the target orientation. Furthermore, the orientation feedback device 36 can include a visual feedback device 40 that emits a visual feedback signal. For instance, the visual feedback device 40 can include one or more lights, such as LED lights, for emitting a preprogrammed light pattern when the impactor tool 16 is in the target orientation. Additionally, the orientation feedback device 36 can include a tactile feedback device that selectively emits a tactile feedback signal when the impactor tool 16 is in the target orientation. For instance, the tactile feedback device 42 can include a vibration motor that selectively vibrates the housing 28 and the impactor tool 16 when the impactor tool 16 is in the target orientation.

It will be appreciated that the orientation feedback device 36 can provide any suitable feedback signal. Also, it will be appreciated that the feedback signal can be seen, heard, and felt simultaneously, and this redundancy can increase accuracy and convenience. Thus, for instance, if the visual feedback device 40 becomes covered in blood or tissue during use, the audible and/or tactile feedback device 38, 42 can adequately provide the feedback signal. However, it will be appreciated that the orientation feedback device 36 can include any number of feedback devices 38, 40, 42 or any other suitable feedback device without departing from the scope of the present disclosure.

Moreover, as illustrated in FIG. 4, the implanting apparatus 26 can include a controller 46. The controller 46 can include various components, such as a microprocessor, memory, and the like. The controller 46 can be encapsulated within the housing 28 of the implanting apparatus 26, or the controller 46 can be at least partially provided in a remote device, such as a separate computerized system. The controller 46 can be in communication with the orientation sensor 34 and the orientation feedback device 36. Accordingly, as will be discussed, the controller 46 causes the orientation feedback device 36 to selectively provide the respective orientation feedback signal(s) when the actual orientation of the impactor tool 16 detected by the orientation sensor 34 is substantially equal to a predetermined target orientation of the impactor tool 16.

More specifically, with reference to FIG. 3, the medical professional can analyze the pelvis 15 and other anatomical features of the patient 19 to determine a desired final, target location (i.e., target position, target orientation) for the acetabular cup 14 within the acetabulum 17, which will provide the patient 19 with sufficient stability, support, etc. The implanting assembly 10 can be used to properly orient the impactor tool 16 such that the impactor tool 16 accurately drives the acetabular cup 14 toward this desired target location. For instance, the surgeon can predetermine how the load axis A of the impactor tool 16 should be oriented relative to a reference coordinate system such that the impactor tool 16 drives the acetabular cup 14 into the predetermined target location. For purposes of discussion, this will be referred to as the predetermined target orientation of the impactor tool 16. It will be appreciated that the target orientation of the impactor tool 16 substantially corresponds to the trajectory or path of the acetabular cup 14 as it is driven into the acetabulum 17 by the impactor tool 16.

As shown in FIG. 3, the predetermined target orientation of the impactor tool 16 can be the orientation of the load axis A relative to a median plane $P_m$ (i.e., sagittal plane) and a coronal plane $P_c$ (i.e., frontal plane) of the patient 19. Specifically, the surgeon can determine a particular target inclination angle $\theta_i$ of the load axis A relative to the median plane $P_m$ and/or a particular anteversion angle $\theta_a$ of the load axis A relative to the coronal plane $P_c$ necessary for the impactor tool 16 to drive the acetabular cup 14 into the final location within the pelvis 19.

It will be appreciated that the predetermined target orientation can be expressed as a range of values. In some embodiments, for instance, the target inclination angle $\theta_i$ is at least approximately 35° and at most approximately 55°. Also, in some embodiments, the target anteversion angle $\theta_a$ is at least 10° and at most 20°. Furthermore, in some embodiments, the target inclination angle $\theta_i$ is approximately 45°. Additionally, in some embodiments, the target anteversion angle $\theta_a$ is approximately 15°. As will be discussed, the implanting apparatus 26 can include one or more selectable preprogrammed target orientations, which is/are stored in memory, and/or the predetermined target orientation can manually set by the user.

It will be appreciated that the target inclination and anteversion angles $\theta_i$, $\theta_a$ can be determined for each individual patient 19 according to the anatomical structure of the patient 19 and/or other factors. It will also be appreciated that the target inclination and anteversion angles $\theta_i$, $\theta_a$ can be of any suitable values. Furthermore, it will be appreciated that the implantation assembly 10 can be used to detect and confirm any suitable orientation of the impactor tool 16 relative to any suitable reference plane, axis, etc. It will be appreciated that the reference plane, axis, etc. can be separate from the patient 19, or in other embodiments, the reference plane, axis, etc. can be associated directly with the anatomy of the patient 19. For instance, the surgeon can input the location, orientation, etc. of certain anatomical features into a computerized system, and this data can be used as reference data or as a coordinate system to detect the actual orientation of the impactor tool 16 as will be discussed.

Thus, to implant the acetabular cup 14, the surgeon dislocates the hip joint of the patient 19, performs any necessary reaming of the acetabulum 17 of the patient 19, and mounts the acetabular cup 14 to the impactor tool 16 as discussed above. The surgeon also determines the target inclination angle $\theta_i$, and the anteversion angle $\theta_a$ of the impactor tool 16. Then, as the surgeon moves the impactor tool 16 generally into position to implant the cup 14, the orientation sensor 34 detects the actual orientation of the load axis A of the impactor tool 16. The orientation feedback device 36 provides one or more feedback signals when the load axis A is substantially aligned with the predetermined target inclination angle $\theta_i$ and the predetermined target anteversion angle $\theta_a$. Once the feedback signals are provided, the surgeon knows that the impactor tool 16 is properly oriented, and the surgeon can begin applying the load $F_i$ to the head 20 of the impactor tool 16, thereby driving the cup 14 into the acetabulum 17 of the patient 19.

It will be appreciated that the implanting apparatus 26 can be configured to detect any suitable orientation other than the inclination angle $\theta_i$ and the anteversion angle $\theta_a$. Also, it will be appreciated that the orientation feedback device 36 can provide separate feedback signals for the inclination angle $\theta_i$ and the anteversion angle $\theta_a$. Furthermore, the implanting apparatus 26 can store in memory one or more default target inclination angles $\theta_i$ and/or target anteversion angles $\theta_a$.

Additionally, in some embodiments, the implanting apparatus 26 can include various controls for manually setting the target inclination angle $\theta_i$ and/or target anteversion angle $\theta_a$. For instance, the implanting assembly 10 can include an input device 41 (FIGS. 1 and 4) for manually setting the target orientation of the impactor tool 16. More specifically, the input device 41 can include buttons, dials, a display, and other features for setting the target inclination angle $\theta_i$, the target anteversion angle $\theta_a$, or any other setting for the implanting assembly 10. The input device 41 can be integrally coupled to the housing 28, and/or the input device 41 can be separate and remote from the housing 28 of the apparatus 26. For instance, the input device 41 can be in wireless communication with the implanting apparatus 26. For instance, as shown in FIG. 1, the input device 41 can include a wireless transmitter 43, and the implanting apparatus 26 can include a wireless receiver 45. The receiver 45 receives wireless signals from the transmitter 43 to thereby set the target orientation of the load axis A. For instance, the input device 41 can include a switch for choosing between multiple (e.g., three) different preset target orientations (e.g., a first non-adjustable range, a second non-adjustable range, and a third non-adjustable range). Also, in some embodiments, the input device 41 can include an alphanumeric keypad for manually inputting and setting a particular target orientation.

Furthermore, in some embodiments, the input device 41 can include the orientation feedback device 36. For instance, the input device 41 can include a speaker of the audible feedback device 38 or any other suitable component of the orientation feedback device 36.

Thus, the implanting apparatus 26 can allow the surgeon to implant the acetabular cup 14 more conveniently and with greater accuracy. It will be appreciated that the implanting apparatus 26 can provide feedback to the surgeon before the input load $F_i$ is applied and while the acetabular cup 14 is being driven into the acetabulum 17. Accordingly, the acetabular cup 14 can be more easily and accurately placed into the target location within the pelvis 15.

However, it can be difficult for the surgeon to know when the acetabular cup 14 is fully seated in the pelvis 15. Thus, the implanting apparatus 26 can further include an impact sensor 47 (FIGS. 1, 2 and 4). As will be described, the impact sensor 47 can detect an actual effect of impacting the impactor tool 16. For instance, the impact sensor 47 can be configured to detect an actual impact force $F_i$ on the head 20 of the impactor tool 16. Furthermore, the impact sensor 47 can detect an actual displacement of the impactor tool 16 when the load $F_i$ is applied to the head 20. In addition, the impact sensor 47 can detect an actual acoustic effect occurring when the load $F_i$ is applied. It will be appreciated that the impact sensor 47 can be configured to detect any suitable effect of applying the load $F_i$. The impact sensor can include any suitable component, such as an accelerometer and/or a piezoelectric sensor, for detecting the actual impact effect. It will be appreciated that the orientation sensor 34 and the impact sensor 47 can rely on the same components, such as a common accelerometer, for the respective functions.

In addition, the implanting apparatus 10 can include an impact feedback device 48 (FIG. 4). Generally, the impact feedback device 48 provides a feedback signal when the actual effect of applying the load $F_i$ detected by the impact sensor 47 substantially matches a predetermined target impact effect. More specifically, as will be discussed, the surgeon can predetermine a target impact effect (e.g., a predetermined impact force $F_i$, an amount of displacement, an acoustic effect, etc.) that correlates to a condition in which the acetabular cup 14 is fully seated in the acetabulum 17. Then, the controller 46 can cause the impact feedback device 48 to provide the respective feedback signal when the actual impact effect substantially matches the predetermined target impact effect. Thus, the impact feedback device 48 can inform the surgeon that the acetabular cup 14 has been driven sufficiently deep enough into the acetabulum 17 of the patient 19.

More specifically, when the acetabular cup 14 is driven into the acetabulum 17 and hits cortical bone, the amount of bounce back (i.e., displacement) of the impactor tool 16 in a direction opposite to the vector of the load $F_i$ may change significantly. This predetermined amount of displacement can be stored in memory as the target impact effect of applying the load $F_i$, and the impact feedback device 48 can provide the feedback signal when the actual displacement of the impactor tool 16 is substantially equal to or exceeds the target displacement, thereby indicating that the acetabular cup 14 has reached the cortical bone of the pelvis 15. Likewise, the target impact effect can be a predetermined threshold amount of force, acoustic effect, or any other suitable target effect indicative of the acetabular cup 14 impacting the cortical bone. Moreover, in some embodiments, the input device 41 can be used to manually select a preset target impact effect or to manually set an individual target impact effect as discussed above.

It will be appreciated if the impact feedback device 48 can include any suitable device, such as an audible feedback device 50, a visual feedback device 52, and/or a tactile feedback device 54. The audible feedback device 50 provides an audible feedback signal, and can include a speaker or any other suitable device for providing an audible feedback signal. The visual feedback device 52 provides a visual feedback signal, and can include one or more lights, such as LED lights, for providing a visual feedback signal. Also, the tactile feedback device 54 provides a tactile feedback signal and can include a vibration motor that selectively provides a tactile feedback signal.

Figure 5:
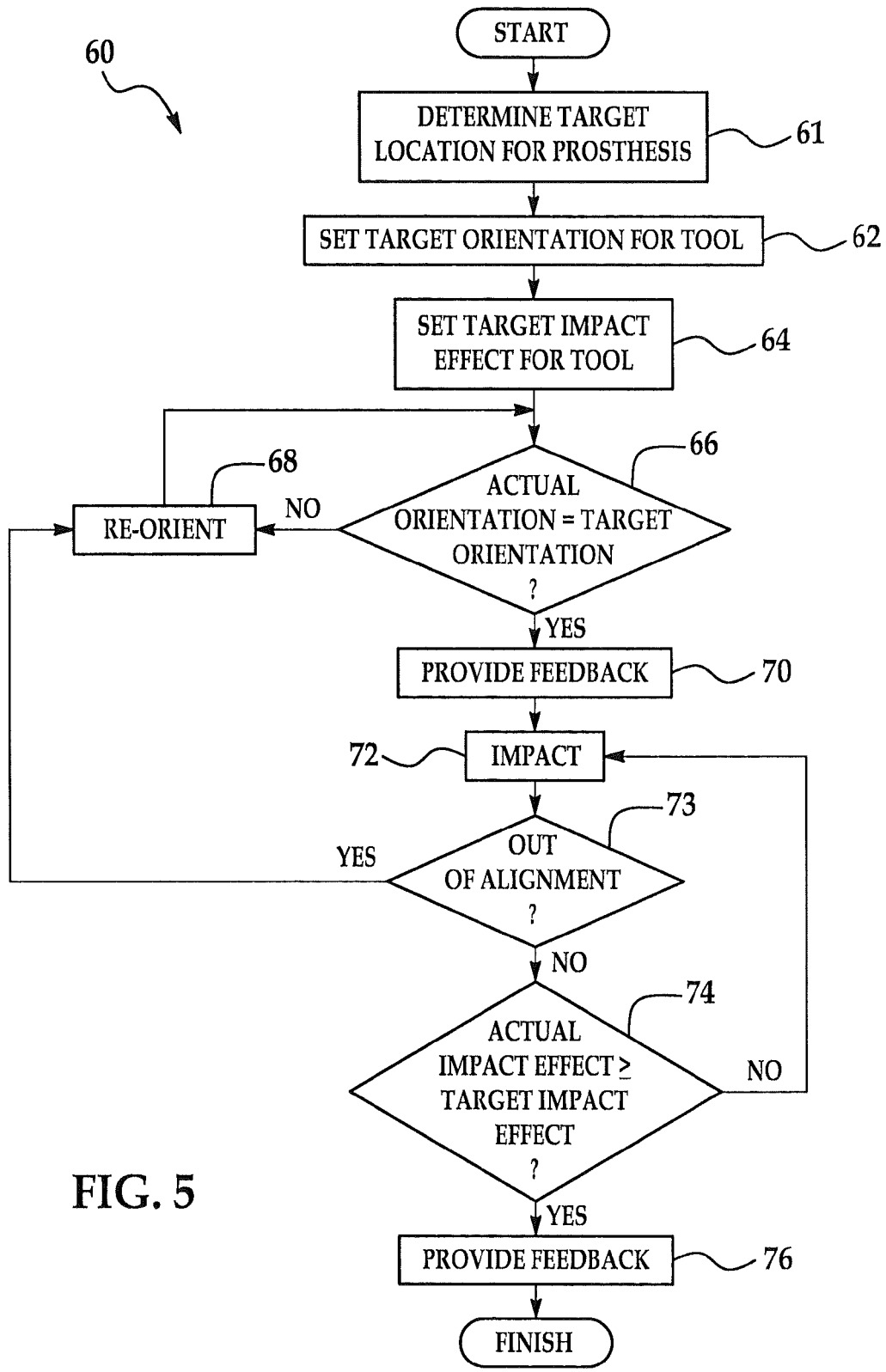
FIG. 5 is a flowchart illustrating a method of implanting a prosthetic implant using the implanting assembly of FIG. 1.

Thus, referring to FIG. 5, an exemplary embodiment of a method of implanting the acetabular cup 14 will be discussed in greater detail. The method 60 begins in block 61, in which the target location of the acetabular cup 14 is determined. More specifically, the surgeon analyzes the pelvis 15 and other anatomical features of the patient 19 and determines where the acetabular cup 14 should be implanted (i.e., the target location of the acetabular cup 14) within the acetabulum 17. Block 61 can include selecting a particular inclination angle $\theta_i$ and/or a particular anteversion angle $\theta_a$ of the axis A of the acetabular cup 14.

Then, in block 62, the surgeon determines a target orientation for the impactor tool 16 necessary to drive the acetabular cup 14 into the target location determined in block 61. As discussed above, the surgeon can use the input device 41 to manually input a target orientation for the impactor tool 16, or the surgeon can use the input device 41 to select one of the various default target orientations for the impactor tool 16. Also, the input device 41 can automatically calculate and set the target orientation of the impactor tool 16 based on various parameters input by the surgeon. In some embodiments, the target orientation can be set to any suitable value(s) for high precision.

Furthermore, in block 64, the surgeon determines a target impact effect for the impactor tool 16. As discussed above, the input device 41 can be used to set the target impact effect necessary for achieving the target location selected in block 61. Also, the surgeon can use the input device 41 to select one of the various default target impact effects, or the input device 41 can automatically calculate and set the target impact effect based on various parameters input by the surgeon. Moreover, the target impact effect can be set to any suitable value(s) for high precision.

Then, as the surgeon moves the impactor tool 16, it is determined in decision block 66 whether the actual orientation of the load axis A is substantially equal to or within the predetermined range of the target orientation set in block 62. If the actual orientation is substantially equal to or within the range of the target orientation, then in block 70, the orientation feedback device 36 provides the respective feedback signal(s) described above. However, if the actual orientation does not substantially equal or is outside the range of the target orientation, then in block 68, the surgeon re-orients the impactor tool 16 until the actual orientation is substantially equal to or within the range of the target orientation (i.e., decision block 66 answered affirmatively) and the orientation feedback signal(s) is/are provided.

Then, in block 72, the surgeon begins applying the load $F_i$ to the head 20 of the impactor tool 16. The load $F_i$ can be applied with a manual tool, such as a mallet, or an automated tool can be used to apply the load $F_i$.

In some embodiments, the surgeon strikes the head 20 of the impactor tool 16 repeatedly to progressively drive the cup 14 deeper into the acetabulum 17. Because each impact may cause the impactor tool 16 to move out of alignment with the target orientation set in block 62, the method 60 includes decision block 73, wherein it is determined whether the load axis A of the impactor tool 16 has moved out of alignment from the target orientation. If decision block 73 is answered affirmatively, block 68 follows, and the surgeon reorients the impactor tool 16 until the load axis A is substantially aligned with the target orientation. Once the impactor tool 16 is properly reoriented, the feedback signal is again provided in block 70, and the surgeon can continue to impact the tool 16. However, assuming that the actual orientation of the load axis A remains in alignment with the target orientation set in block 62 (i.e., decision block 73 answered negatively), decision block 74 follows.

In decision block 74, it is determined whether the actual impact effect substantially matches or exceeds a threshold of the target impact effect set in block 64. If the actual impact effect is substantially different from the target impact effect, then block 72 occurs, and the surgeon further applies the load $F_i$ supplied to the head 20 of the impactor tool 16. However, once the impact sensor 47 detects that the actual impact effect substantially matches or exceeds the target impact effect, then the impact feedback device 48 provides the respective feedback signal in block 76, and the surgeon is aware that the cup 14 is in the target location predetermined in block 61. It will be appreciated that the impact feedback signal can be provided simultaneously with the orientation feedback signal so that the surgeon knows that the acetabular cup 14 is correctly located in the desired target location within the acetabulum 17.

In some embodiments, once the feedback signals have been provided, they can be manually turned off. For instance, if the feedback signal is a light, then the surgeon has the ability to turn off the light. Thus, the surgeon has greater control over the feedback signal. Also, if the surgeon wishes to re-confirm that the impactor tool 16 is properly oriented or that the acetabular cup 14 is properly seated, the surgeon can turn off the respective feedback signal and check whether the feedback signal is provided again.

Accordingly, the implanting assembly 10 provides a convenient and accurate means for orienting the impactor tool 16 and for implanting the acetabular cup 14. The implanting assembly 10 also ensures that the acetabular cup 14 will be seated in the desired location within the pelvis 15. As such, the prosthetic joint assembly is more likely to provide adequate support and stability to the patient 19.

Figure 6:
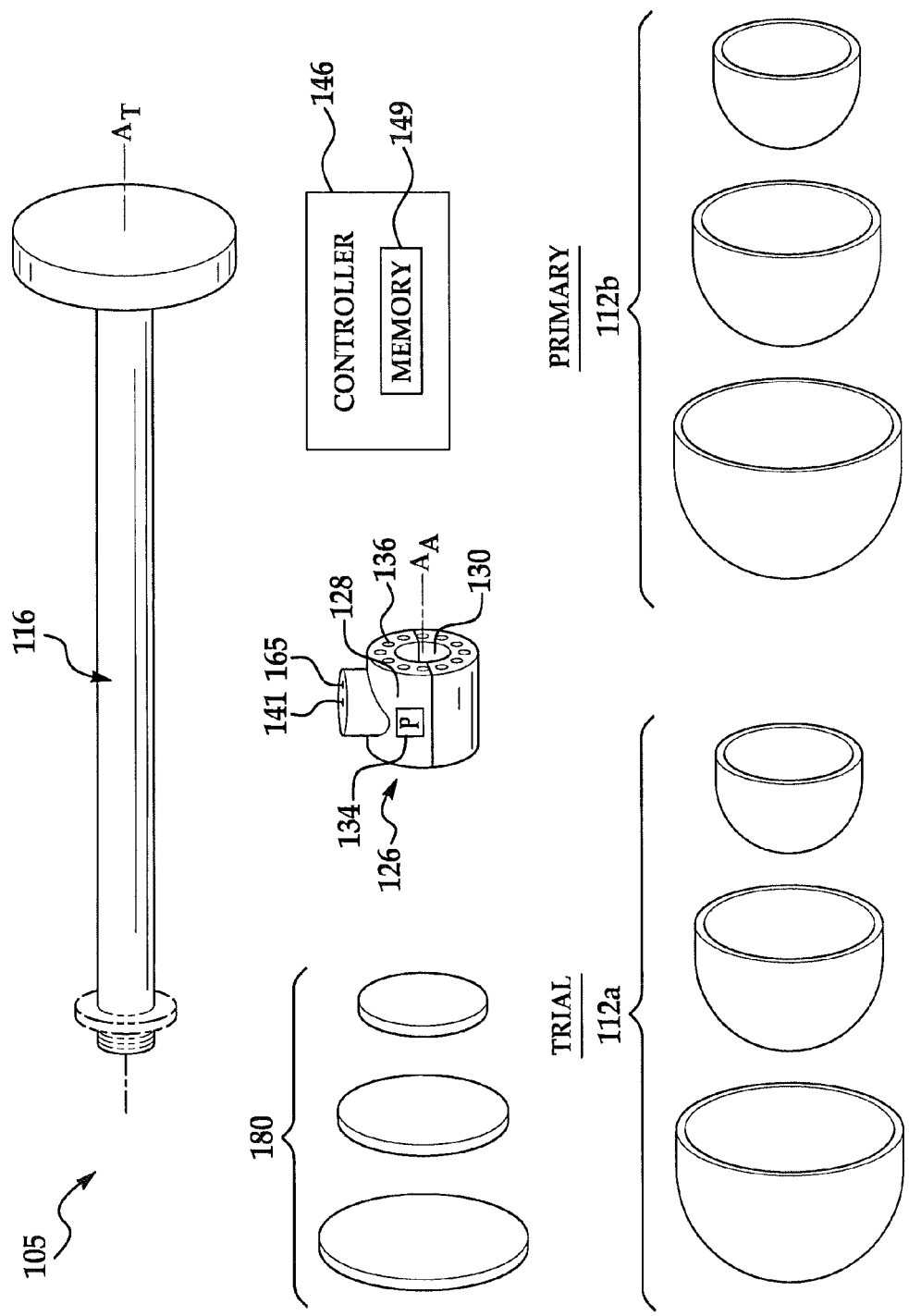
FIG. 6 is a perspective view of a system for implanting a prosthesis according to various other exemplary embodiments of the present disclosure.

Referring now to FIG. 6, another exemplary embodiment of a prosthesis implantation system 105 is illustrated. As will be discussed in greater detail, the system 105 can include various components that are similar to those discussed above. Components that are similar to the embodiments of FIGS. 1-5 are identified with corresponding reference numerals increased by 100. As will be discussed, the system 105 can be a modular kit that facilitates the selection and implantation of a prosthetic device, such as a prosthetic hip joint.

In some embodiments, the system 105 can include an impactor tool 116 of the type discussed above and shown in FIGS. 1 and 2. Also, the system 105 can include an implanting apparatus 126 of the type discussed above and shown in FIGS. 1 and 2. As such, the implanting apparatus 126 can include a housing 128. The housing 128 can be tubular and can include a passage 130 or other type of aperture extending therethrough. Furthermore, the implanting apparatus 126 can include an orientation sensor 134 that is in communication with a controller 146 of the type discussed above. As stated above, the orientation sensor 134 can include an accelerometer (e.g., a three-axis accelerometer) that, with the controller 146, detects an actual orientation of the housing 128 relative to a reference point, vector, axis, etc. For instance, in some embodiments, the orientation sensor 134 can detect an actual orientation of the axis $A_A$ of the housing 128 relative to a direction of gravity. In other embodiments, the orientation sensor 134 is calibrated in order to detect the orientation of the axis $A_A$ relative to another reference system, such as medical equipment used during implantation procedures (e.g., an examination table, etc.), the patient's anatomy, and the like.

The controller 146 can be embedded and housed within the housing 128. Also, in some embodiments, the controller 146 can be independent of the housing 128, and the orientation sensor 134 can be in wired or wireless communication with the controller 146. In still other embodiments, some components of the controller 146 can be enclosed within the housing 146 and other components of the controller 146 can be independent of the housing 146.

The controller 146 can include a memory module 149. The memory module 149 can be of any suitable type, such as computer-readable random access memory (RAM).

Also, the implanting apparatus 126 can include an input device 141. The input device 141 can include one or more buttons, switches, etc. that the user can press, slide, actuate, or otherwise manipulate for selectively providing a user input. As will be discussed in greater detail below, the user can use the input device 141 to cause the actual orientation of the axis $A_A$ detected by the orientation sensor 134 to be stored in the memory module 149. This stored data can be referenced later as a target orientation of the housing 128 while implanting a prosthetic member.

Additionally, the implanting apparatus 126 can include an orientation feedback device 136 of the type discussed above in relation to FIGS. 1-5. As such, the orientation feedback device 136 can include a visual feedback device (e.g., one or more LED lights) that emits a visual feedback signal, an audible feedback device (e.g., an audible alarm) that emits an audible feedback signal, and/or a tactile feedback device (e.g., a vibratory motor) that emits a tactile feedback signal. As will be discussed, the orientation feedback device 136 can emit the respective feedback signal(s) when the orientation of the axis $A_A$ substantially matches the target orientation stored in the memory module 149.

As discussed above, the passage 130 can receive the impactor tool 116 to thereby removably couple the implanting apparatus 126 to the impactor tool 116. When coupled, the orientation sensor 134 can detect an actual orientation of the impactor tool 116. For instance, the orientation sensor 134 can detect an actual orientation of the axis $A_T$ of the impactor tool 116.

In some embodiments, the implanting apparatus 126 and the impactor tool 116 can be coaxial. In other embodiments, the respective axes $A_A$, $A_T$ can be spaced apart. Also, calibration of the orientation sensor 134 may be necessary such that the orientation sensor 134 can be used to accurately detect the orientation of the impactor tool 116.

Figure 9:
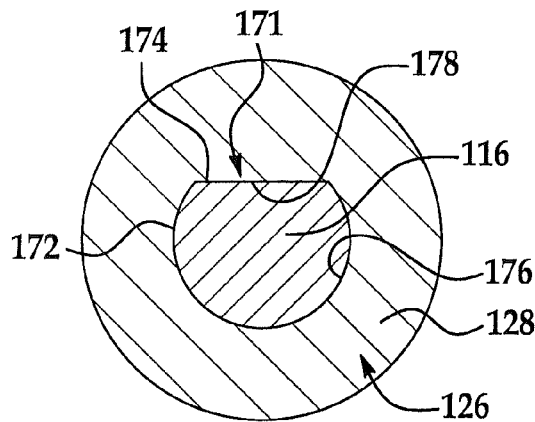
FIG. 9 is a section view of an impactor tool and an implanting apparatus of FIG. 6.

Furthermore, the housing 128 of the implanting apparatus 126 and/or the impactor tool 116 can include a keying feature 171 as shown in FIG. 9. The keying feature 171 allows the housing 128 to be coupled to the impactor tool 116 only at a known orientation. For instance, the impactor tool 116 can include a rounded surface 172 and a flat surface 174. Similarly, the housing 128 can include a rounded surface 176 and a flat surface 178. The flat surfaces 174, 178 can abuttingly mate such that the axis $A_A$ is at a known orientation relative to the axis $A_T$. It will be appreciated that the housing 128 and impactor tool 116 can include any suitable features for keying the housing 128 to the impactor tool 116 without departing from the scope of the present disclosure.

In addition, the housing 128 of the implanting apparatus 126 can include a visual indicator 165. The visual indicator 165 can be of any suitable type, such as a laser-etched mark or other indicia. The visual indicator 165 can allow the user to visually confirm that the housing 128 (and thus the axis $A_A$) is at a known and predetermined orientation relative, for instance, to the direction of gravity.

The system 105 can further include a plurality of prosthetic members 112a, 112b, such as prosthetic acetabular cups for a prosthetic hip joint. It will be appreciated that the prosthetic members 112a, 112b can be of any suitable type. The prosthetic members 112a, 112b can vary in size, structural features, materials, or in any other suitable manner.

In some embodiments, the prosthetic members 112a, 112b within the system 105 can include a plurality of trial prosthetic members 112a and a plurality of primary and/or revision prosthetic members 112b. The trial prosthetic members 112a can each have a primary prosthetic member 112b that corresponds in size, structural features, and the like. Also, as will be discussed, the trial prosthetic members 112a can be used to select and prepare for implanting one of the primary prosthetic members 112b. As such, the medical professional can experiment with the trial prosthetic members 112a to determine which of the primary prosthetic members 112b to implant into the patient. Also, with the trial prosthetic member 112a, the medical professional can determine and select a target orientation for implanting the primary prosthetic member 112b as will be discussed in greater detail below.

The housing 128 of the implanting apparatus 126 can be removably coupled to each of the trial prosthetic members 112a. For these purposes, the system 105 can include one or more coupling members 180. The coupling members 180 can be substantially disc-shaped and can have a variety of sizes according to sizes of corresponding trial prosthetic members 112a.

Figure 7:
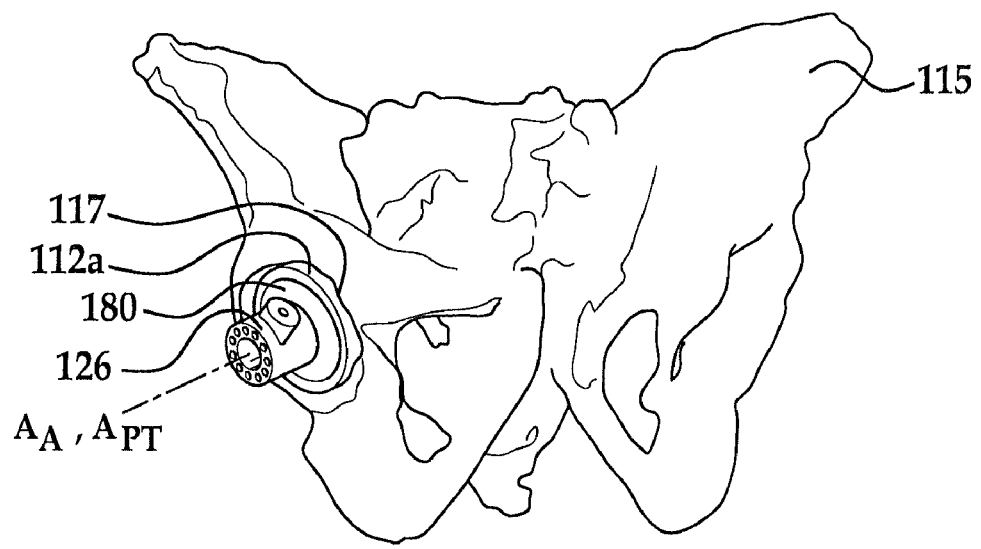
FIG. 7 is a perspective view of a prosthesis implanting apparatus coupled to a trial prosthetic implant of FIG. 6, shown relative to a pelvis.

The coupling members 180 can removably couple to the trial prosthetic members 112a as shown in FIG. 7. For instance, the coupling member 180 can be received within the trial prosthetic member 112a to be coupled thereto. Also, the trial prosthetic member 112a can include a continuous groove (not shown) that removably receives the coupling member 180; however, it will be appreciated that the coupling member 180 can be coupled to the trial prosthetic member 112a in any suitable fashion. Furthermore, the coupling member 180 can be integrally coupled to the trial prosthetic member 112a so as to be monolithic.

The implanting apparatus 126 can also removably couple to the coupling member 180. For instance, the implanting apparatus 126 can be threadably coupled to the coupling member 180 or by a snap fit. In other embodiments, the implanting apparatus 126 can be integrally coupled to the coupling member 180 via a breakable joint (not shown), and the user can manually snap and break the coupling member 180 away from the implanting apparatus 126. However, it will be appreciated that the implanting apparatus 126 can be coupled to the coupling member 180 in any suitable fashion.

It will be appreciated that once coupled, the axis $A_A$ of the implanting apparatus 126 can be coaxial with an axis $A_{PT}$ of the trial prosthetic member 112a as shown in FIG. 7. Thus, by detecting the orientation of the axis $A_A$, the orientation sensor 134 can detect the orientation of the axis $A_{PT}$ of the trial prosthetic member 112a. In other embodiments, the axis $A_A$ can be spaced apart from the axis $A_{PT}$, but because the relative position of the axes $A_A$, $A_{PT}$ is known, the orientation sensor 134 can detect the orientation of the axis $A_{PT}$ when the implanting apparatus 126 is coupled to the trial prosthetic member 112a.

Figure 8:
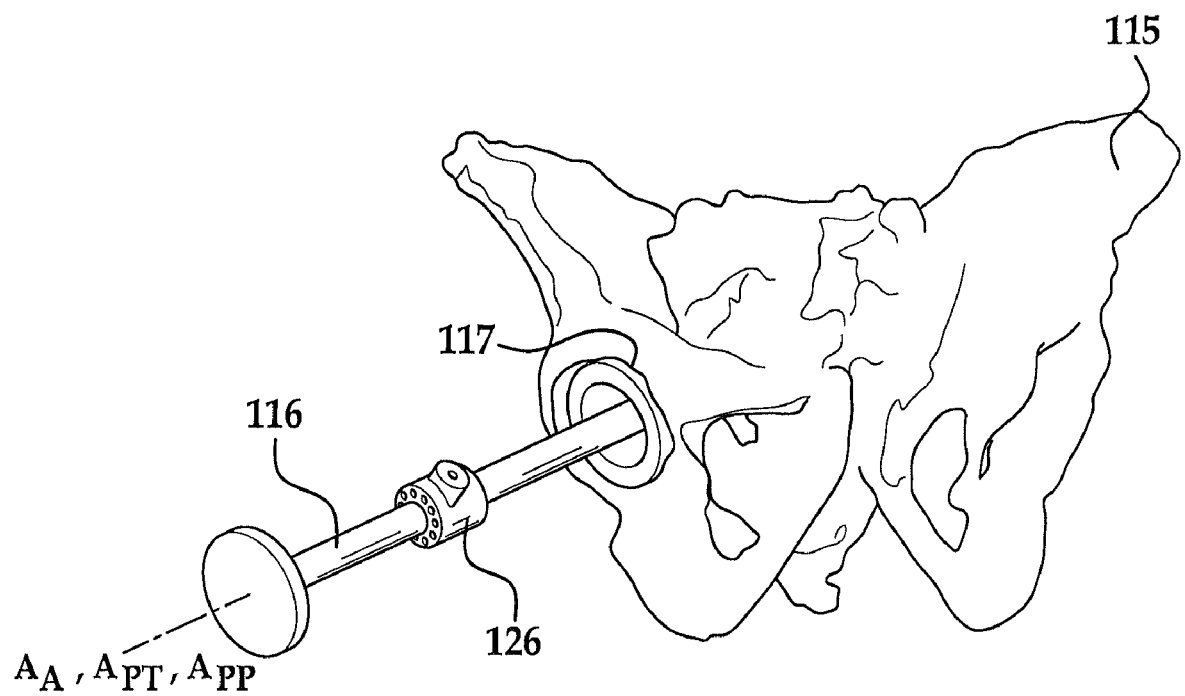
FIG. 8 is a perspective view of the prosthesis implanting apparatus of FIG. 7 coupled to a primary prosthetic implant of FIG. 6.

The implanting apparatus 126 can also be coupled to the primary prosthetic members 112b. For instance, as shown in FIG. 8 and similar to the embodiments of FIGS. 1 and 2, the impactor tool 116 can couple to one of the prosthetic members 112b, and the implanting apparatus 126 can removably couple to the impactor tool 116. Also, in some embodiments, the coupling member 180 includes an aperture (not shown) that receives the impactor tool 116 so that the coupling member 180 can remain attached to the implanting apparatus 126 when the implanting apparatus 126 is coupled to the impactor tool 116. It will be appreciated that once coupled, the orientation of the axis $A_A$ of the implanting apparatus 126 is known relative to an axis $A_T$ of the impactor tool 116 and the axis $A_{PP}$ of the primary prosthetic member 112b as shown in FIG. 8. For instance, these axes $A_A$, $A_{PT}$, $A_{PP}$ can be substantially aligned. Thus, by detecting the orientation of the axis $A_A$, the orientation sensor 134 can detect the orientation of the axes $A_{PT}$, $A_{PP}$ as well.

Figure 10:
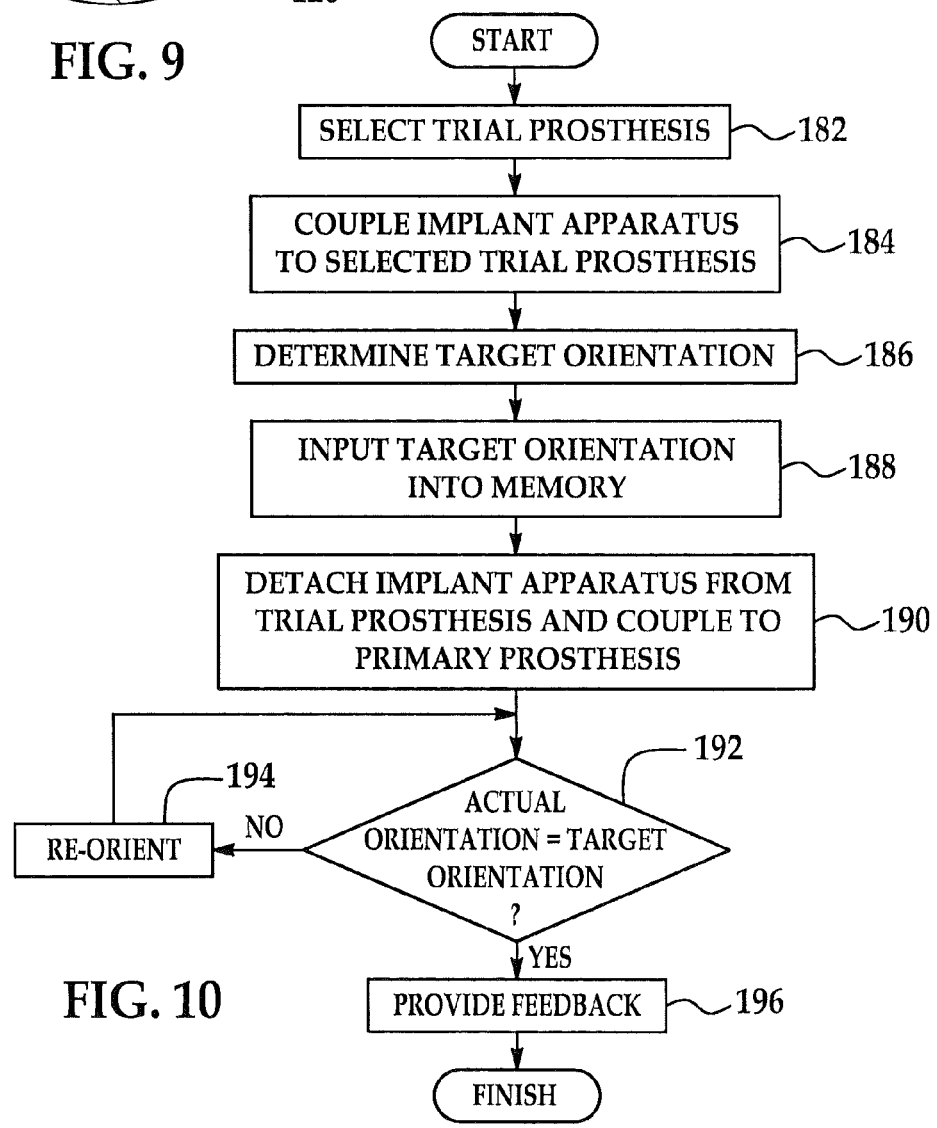
FIG. 10 is a flow-chart illustrating a method of using the system of FIG. 6. to implant the primary prosthetic implant.

Thus, referring now to FIG. 10, a method of using the system 105 will be discussed. Beginning in step 182, the medical professional can select a trial prosthetic member 112a from the plurality of trial prosthetic members 112a within the system 105. As stated above, the trial prosthetic member 112a can be selected according to the size, material, etc. needed for a particular patient and to properly trial the implant relative to the patient's anatomy.

Then, in step 184, the implanting apparatus 126 can be coupled to the selected trial prosthetic member 112a. As stated above and as shown in FIG. 7, the implanting apparatus 126 can be coupled to the member 112a via a corresponding coupling member 180. Also, the implanting apparatus 126 can be coupled relative to the trial prosthetic member 112a such that the visual indicator 165 is at a known location, for instance, relative to the direction of gravity. Furthermore, the implanting apparatus 126 can be coupled such that the axis $A_A$ of the implanting apparatus 126 is at a known orientation relative to the axis $A_{PT}$ of the trial prosthetic member 112a.

Next, in step 186, the medical professional can determine the target orientation for subsequently implanting one of the primary prosthetic members 112b. For instance, as shown in FIG. 7, the medical professional can manipulate and move the trial prosthetic member 112a and the attached implanting apparatus 126 relative to a reamed acetabulum 117 of the patient's pelvis 115. As such, the medical professional can find a desired (i.e., target) orientation to be used when implanting the primary prosthetic member 112b. It will be appreciated that the medical professional can rely on separate measuring devices or any other means for determining the target orientation.

Once the target orientation has been determined in step 186, step 188 follows, and the medical professional can manipulate the input device 141 included on the implanting apparatus 126. The orientation of the axes $A_A$, $A_{PT}$ detected at this time is, in turn, transferred into memory in the memory module 149. Thus, this stored initial orientation is manually inputted by the medical professional and, as will be discussed, this stored initial orientation represents a target orientation for use when implanting the primary prosthetic member 112b within the pelvis 115.

Next, in step 190, the implanting apparatus 126 is detached from the trial prosthetic member 112a. Also, in step 190, the implanting apparatus 126 is coupled to the primary prosthetic member 112b. For instance, the primary prosthetic member 112b corresponding to the trial prosthetic member 112a selected in step 182 can be coupled to the impactor tool 116, and the implanting apparatus 126 can be coupled to the impactor tool 116 as well (FIG. 8). It will be appreciated that, once coupled, the orientation sensor 134 can simultaneously detect the orientation of the axis $A_A$, the orientation of the axis $A_T$, and the orientation of the axis $A_{PP}$ of the attached prosthetic member 112b.

Then, the medical professional can begin implanting the prosthetic member 112b. The orientation sensor 134 continuously monitors the actual orientation of the apparatus 126, the impactor tool 116, and the prosthetic member 112b, and this information is provided to the user via the feedback device 136. More specifically, in decision block 192, it can be determined whether the actual orientation (i.e., the implanting orientation) is substantially equal to the target orientation saved in step 188 based on whether or not the feedback device 136 is emitting its feedback signal. If not, then in step 194, the medical professional knows to re-orient the impactor tool 116. However, once the actual orientation substantially matches the target orientation, the feedback device 136 provides the feedback signal in step 196. As such, the medical professional knows to start applying a load to the impactor tool 116 to drive and implant the prosthetic member 112b into the pelvis 115.

It will be appreciated that the system 105 can be adapted to additionally provide feedback when the prosthetic member 112b has reached its fully impacted or fully seated position within the pelvis 115 as discussed above. For instance, once the prosthetic member 112b reaches cortical bone, the system 105 can provide a corresponding feedback signal.

Accordingly, the system 105 provides a convenient and accurate means for detecting and saving a target orientation for the prosthetic member 112b within the pelvis 115. The system 105 also conveniently provides feedback to the medical professional so that the prosthetic member 112b is properly oriented during implantation. As such, the prosthetic member 112b is more likely to provide adequate support and stability for the patient over the lifetime of the prosthetic joint.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A surgical instrument for implanting a primary prosthetic member in an anatomical feature based on information gained using a trial prosthetic member, the trial prosthetic member substantially corresponding in size and structure to the primary prosthetic member, the surgical instrument comprising:
   an orientation sensor that detects a trial orientation of the trial prosthetic member, the orientation sensor also operable to detect an actual orientation of the primary prosthetic member;
   a memory module;
   an input device that receives a user input to transfer the trial orientation of the trial prosthetic member detected by the orientation sensor into the memory module for storage when the trial orientation corresponds to a target orientation necessary for moving and implanting the primary prosthetic member into engagement with the anatomical feature;
   an orientation feedback device that selectively provides an orientation feedback signal to a user; and
   a controller that causes the orientation feedback device to provide the orientation feedback signal when the actual orientation of the primary prosthetic member detected by the orientation sensor is substantially equal to the trial orientation stored in the memory module.

2. A surgical instrument for implanting a primary prosthetic member in an anatomical feature based on information gained using a trial prosthetic member, the trial prosthetic member substantially corresponding in size and structure to the primary prosthetic member, the surgical instrument comprising:
   an orientation sensor that detects an initial orientation of the trial prosthetic member when the trial prosthetic member is oriented as desired relative to the anatomical feature, the orientation sensor also operable to detect an implanting orientation of the primary prosthetic member;
   a memory module;
   an input device that receives a user input to transfer the initial orientation of the trial prosthetic member detected by the orientation sensor into the memory module for storage;
   an orientation feedback device that selectively provides an orientation feedback signal to a user;
   a controller that causes the orientation feedback device to provide the orientation feedback signal when the implanting orientation of the primary prosthetic member detected by the orientation sensor is substantially equal to the initial orientation stored in the memory module; and
   a housing that houses the orientation sensor, the housing being removably coupled relative to one of the trial prosthetic member and the primary prosthetic member to position a housing axis of the housing at a known orientation relative to a prosthesis axis of the one of the trial prosthetic member and the primary prosthetic member.

3. The surgical instrument of claim 2, wherein the housing is alternatively and removably coupled relative to both the trial prosthetic member and the primary prosthetic member.

4. The surgical instrument of claim 2, further comprising an impactor tool that removably couples to the primary prosthetic member, wherein the housing removably couples directly to the impactor tool, and further comprising a coupling member that removably couples the housing to the trial prosthetic member.

5. The surgical instrument of claim 2, further comprising an impactor tool that transfers a load along a load axis to the primary prosthetic member to implant the primary prosthetic member, wherein the impactor tool is removably coupled relative to the primary prosthetic member to position the load axis at a known orientation relative to the prosthesis axis, and wherein the housing is removably coupled to the impactor tool to position the housing axis at a known orientation relative to both the load axis and the prosthesis axis.

6. The surgical instrument of claim 5, wherein the housing includes a first portion and a second portion that are hingeably attached so as to have a clam shell construction, and wherein an aperture is defined between the first and second portions, the aperture operable to receive the impactor tool to removably couple to the impactor tool.

7. The surgical instrument of claim 5, wherein the housing includes a visual indicator that indicates a location of the housing axis.

8. The surgical instrument of claim 5, further comprising a keying feature that allows the housing to be coupled to the impactor tool only at the known orientation relative to both the load axis and the prosthesis axis.

9. The surgical instrument of claim 2, wherein the input device is a button that is moveably mounted to the housing.

10. The surgical instrument of claim 1, wherein the orientation sensor includes an accelerometer that detects the trial orientation and the actual orientation of the prosthetic member relative to a direction of gravity.

11. The surgical instrument of claim 1, wherein the orientation feedback device includes at least one of a visual feedback device that emits a visual feedback signal, an audible feedback device that emits an audible feedback signal, and a tactile feedback device that emits a tactile feedback signal.

12. A method of implanting a primary prosthetic member in an anatomical feature based on information gained from a trial prosthetic member that substantially corresponds in size and structure to the primary prosthetic member, the method comprising:
   detecting a trial orientation of the trial prosthetic member;
   saving the trial orientation into a memory module when the trial orientation corresponds to a target orientation necessary for moving and implanting the primary prosthetic member into engagement with the anatomical feature as a result of receiving a user input;
   detecting an actual orientation of the primary prosthetic member; and
   providing an orientation feedback signal when the actual orientation of the primary prosthetic member is substantially equal to the trial orientation saved in the memory module.

13. A method of implanting a primary prosthetic member in an anatomical feature based on information gained from a trial prosthetic member that substantially corresponds in size and structure to the primary prosthetic member, the method comprising:
   detecting an initial orientation of the trial prosthetic member when the trial prosthetic member is oriented as desired relative to the anatomical feature;
   saving the initial orientation into a memory module as a result of receiving a user input;
   detecting an implanting orientation of the primary prosthetic member; and providing an orientation feedback signal when the implanting orientation of the primary prosthetic member is substantially equal to the initial orientation;

wherein detecting the initial orientation of the trial prosthetic member comprises removably coupling a prosthesis implanting apparatus with an orientation sensor to the trial prosthetic member and detecting the initial orientation of the trial prosthetic member with the orientation sensor, and wherein detecting the implanting orientation comprises removably coupling the prosthesis implanting apparatus to the primary prosthetic member and detecting the implanting orientation of the primary prosthetic member with the orientation sensor.

14. The method of claim 13, wherein detecting the implanting orientation further comprises removably coupling an impactor tool to the primary prosthetic member and removably coupling the prosthesis implanting apparatus to the impactor tool.

15. The method of claim 14, further comprising impacting the impactor tool to transfer an impact force via the impactor tool to the primary prosthetic member and to drive the primary prosthetic member toward a target location within a patient.

16. The method of claim 14, wherein removably coupling the prosthesis implanting apparatus to the impactor tool comprises keying the prosthesis implanting apparatus to the impactor tool at a known orientation relative thereto.

17. The method of claim 12, further comprising receiving the user input due to manipulation of an input device by a user.

18. The method of claim 12, further comprising detecting the trial orientation and the actual orientation of the prosthetic member relative to a direction of gravity.

19. A prosthesis implantation system comprising:
a trial prosthetic acetabular cup defining a trial axis;
a primary prosthetic acetabular cup defining a primary axis, the primary prosthetic acetabular cup substantially corresponding in size and structure to the trial prosthetic acetabular cup;
an impactor tool that removably couples to the primary prosthetic acetabular cup and transfers a load along a load axis to implant the primary prosthetic acetabular cup; and
a prosthesis implanting apparatus that includes:
a housing operable to be removably coupled to the trial prosthetic acetabular cup, the housing operable to be alternatively and removably coupled to the impactor tool;
an orientation sensor that detects an initial orientation of the trial axis when the housing is removably coupled to the trial prosthetic acetabular cup and an implanting orientation of the primary axis when the housing is removably coupled to the impactor tool;
a memory module;
an input device that receives a user input to transfer the initial orientation of the trial axis detected by the orientation sensor into the memory module for storage;
an orientation feedback device that selectively provides an orientation feedback signal; and
a controller that causes the orientation feedback device to provide the orientation feedback signal when the housing is coupled to the impactor tool and when the implanting orientation of the primary axis is substantially equal to the initial orientation of the trial axis stored in the memory module.

20. A method of implanting a primary prosthetic acetabular cup in an acetabulum based on information gained from a trial prosthetic acetabular cup that substantially corresponds in size and structure to the primary prosthetic acetabular cup, the method comprising:
removably coupling a prosthesis implanting apparatus with an orientation sensor to the trial prosthetic acetabular cup;
detecting an initial orientation of the trial prosthetic acetabular cup with the orientation sensor when the trial prosthetic member is oriented as desired relative to the acetabulum;
saving the initial orientation of the trial prosthetic member into a memory module as a result of receiving a user input;
removing the prosthesis implanting apparatus from the trial prosthetic acetabular cup;
removably coupling an impactor tool to the primary prosthetic acetabular cup;
removably coupling the prosthesis implanting apparatus to the impactor tool;
detecting an implanting orientation of the primary prosthetic acetabular cup with the orientation sensor when the prosthesis implanting apparatus is removably coupled to the impactor tool and the impactor tool is removably coupled to the primary prosthetic acetabular cup;
providing an orientation feedback signal when the implanting orientation of the primary prosthetic acetabular cup is substantially equal to the initial orientation of the trial prosthetic member; and
implanting the primary prosthetic acetabular cup at the initial orientation.

21. The surgical instrument of claim 1, further comprising an impactor tool that removably couples to the primary prosthetic member, further comprising an impact sensor that detects an actual acoustic effect of impacting the impactor tool, and further comprising an impact feedback device that selectively provides an impact feedback signal, and wherein the controller causes the impact feedback device to provide the impact feedback signal when the actual acoustic effect of impacting the impactor tool detected by the impact sensor substantially matches a predetermined target acoustic effect of impacting the impactor tool.

22. The method of claim 12, further comprising removably coupling an impactor tool to the primary prosthetic member, removably coupling the prosthesis implanting apparatus to the impactor tool, automatically detecting an actual acoustic impact effect of impacting the impactor tool, and automatically providing an impact feedback signal when the actual acoustic impact effect substantially matches a predetermined target acoustic impact effect.

* * * * *